US009392931B2

(12) United States Patent
Urban et al.

(10) Patent No.: US 9,392,931 B2
(45) Date of Patent: Jul. 19, 2016

(54) CONTROLLING A SURGICAL MICROSCOPE

(75) Inventors: Alexander Urban, Forstinning (DE);
Valentin Elefteriu, Tacherting (DE);
Rainer Birkenbach, Erding (DE)

(73) Assignee: Brainlab AG, Feldkirchen (DE)

( * ) Notice: Subject to any disclaimer, the term of this patent is extended or adjusted under 35 U.S.C. 154(b) by 444 days.

(21) Appl. No.: 13/581,519

(22) PCT Filed: Mar. 22, 2010

(86) PCT No.: PCT/EP2010/053654
§ 371 (c)(1),
(2), (4) Date: Aug. 28, 2012

(87) PCT Pub. No.: WO2011/116812
PCT Pub. Date: Sep. 29, 2011

(65) Prior Publication Data
US 2012/0320186 A1 Dec. 20, 2012

(51) Int. Cl.
A61B 17/00 (2006.01)
A61B 90/10 (2016.01)
A61B 34/20 (2016.01)
A61B 1/00 (2006.01)

(52) U.S. Cl.
CPC ... *A61B 1/00149* (2013.01); *A61B 2017/00725* (2013.01); *A61B 2034/2055* (2016.02); *A61B 2090/0818* (2016.02)

(58) Field of Classification Search
CPC .... A61B 19/5223; A61B 19/26; A61B 19/19; A61B 19/5244; A61B 2019/5255; A61B 8/4245; A61B 8/4254; A61B 8/4218; A61B 11/00147; G02B 21/0012; G06T 2210/41

USPC ............. 348/79, 80, 130; 359/368, 372, 382; 250/309, 311; 248/122.1, 123.11
See application file for complete search history.

(56) References Cited

U.S. PATENT DOCUMENTS

| 5,499,097 | A |   | 3/1996  | Ortyn et al. |
|-----------|---|---|---------|--------------|
| 5,524,180 | A | * | 6/1996  | Wang et al. ................... 600/118 |
| 5,795,294 | A |   | 8/1998  | Luber et al. |
| 5,861,983 | A | * | 1/1999  | Twisselman .................. 359/384 |
| 5,982,532 | A |   | 11/1999 | Mittelstadt et al. |
| 6,162,523 | A | * | 12/2000 | Metelski et al. .............. 428/113 |
| 6,456,868 | B2| * | 9/2002  | Saito et al. .................... 600/429 |
| 6,471,165 | B2| * | 10/2002 | Twisselmann ............ 248/123.11 |
| 6,592,086 | B1| * | 7/2003  | Sander ..................... 248/123.11 |

(Continued)

FOREIGN PATENT DOCUMENTS

| DE | 196 39 615 A1 | 4/1998  |
| EP | 1 302 805     | 4/2003  |
| WO | 2008/154935   | 12/2008 |

OTHER PUBLICATIONS

International Search Report for International Application No. PCT/EP2010/053654 dated May 11, 2011.

*Primary Examiner* — Brian Yenke
(74) *Attorney, Agent, or Firm* — Tucker Ellis LLP

(57) ABSTRACT

The invention relates to a method for controlling a surgical microscope (1), wherein the position of the optical system (30) of the microscope (1) is tracked within an operating space by a position tracking system (40), wherein the optical system carrier (20) can be moved by means of a motorized carrier moving system (22, 23, 24). The line of sight of the optical system (30) is automatically set by moving the optical system carrier (20) and is aligned with a predefined direction in said operating space.

23 Claims, 1 Drawing Sheet

(56) References Cited

U.S. PATENT DOCUMENTS

| | | | |
|---|---|---|---|
| 6,661,571 B1* | 12/2003 | Shioda et al. | 359/372 |
| 6,804,547 B2* | 10/2004 | Pelzer et al. | 600/424 |
| 6,914,721 B2* | 7/2005 | Deverin et al. | 359/388 |
| 6,963,444 B2* | 11/2005 | Brenner et al. | 359/384 |
| 7,123,751 B1* | 10/2006 | Fujieda | A61B 5/117 340/5.53 |
| 7,155,316 B2 | 12/2006 | Sutherland et al. | |
| 7,912,532 B2* | 3/2011 | Schmidt et al. | 600/424 |
| 8,396,598 B2* | 3/2013 | Sutherland et al. | 700/264 |
| 2001/0025183 A1* | 9/2001 | Shahidi | 606/130 |
| 2001/0037064 A1* | 11/2001 | Shahidi | 600/429 |
| 2001/0044577 A1* | 11/2001 | Braun et al. | 600/417 |
| 2001/0055062 A1* | 12/2001 | Shioda et al. | 348/79 |
| 2002/0024006 A1 | 2/2002 | Engelhardt | |
| 2002/0105723 A1 | 8/2002 | Bewersdorf et al. | |
| 2003/0090790 A1* | 5/2003 | Metelski | 359/368 |
| 2003/0137723 A1* | 7/2003 | Sander | 359/380 |
| 2004/0010190 A1* | 1/2004 | Shahidi | 600/407 |
| 2004/0036962 A1* | 2/2004 | Brunner et al. | 359/368 |
| 2004/0070822 A1 | 4/2004 | Shioda et al. | |
| 2004/0125437 A1* | 7/2004 | Schmidt et al. | 359/368 |
| 2005/0057800 A1* | 3/2005 | Obrebski et al. | 359/385 |
| 2005/0203374 A1 | 9/2005 | Vilsmeier | |
| 2007/0211243 A1 | 9/2007 | Laroche et al. | |
| 2008/0204864 A1* | 8/2008 | Sander | 359/368 |
| 2008/0303899 A1* | 12/2008 | Berci | 348/74 |
| 2009/0218455 A1* | 9/2009 | Metelski | 248/122.1 |
| 2009/0219613 A1* | 9/2009 | Enge | 359/384 |
| 2009/0316143 A1* | 12/2009 | Yokota et al. | 356/237.5 |
| 2011/0091965 A1* | 4/2011 | Tateyama | 435/287.1 |
| 2012/0184846 A1* | 7/2012 | Izatt et al. | 600/425 |

* cited by examiner

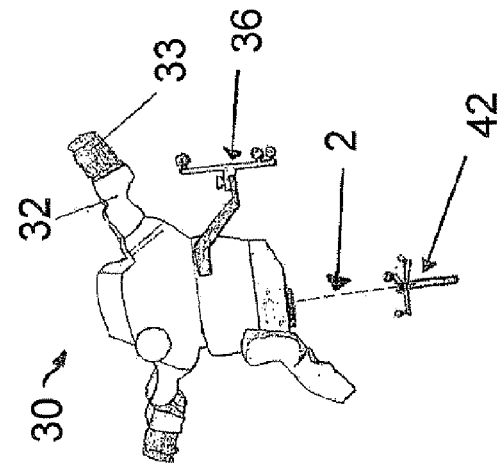
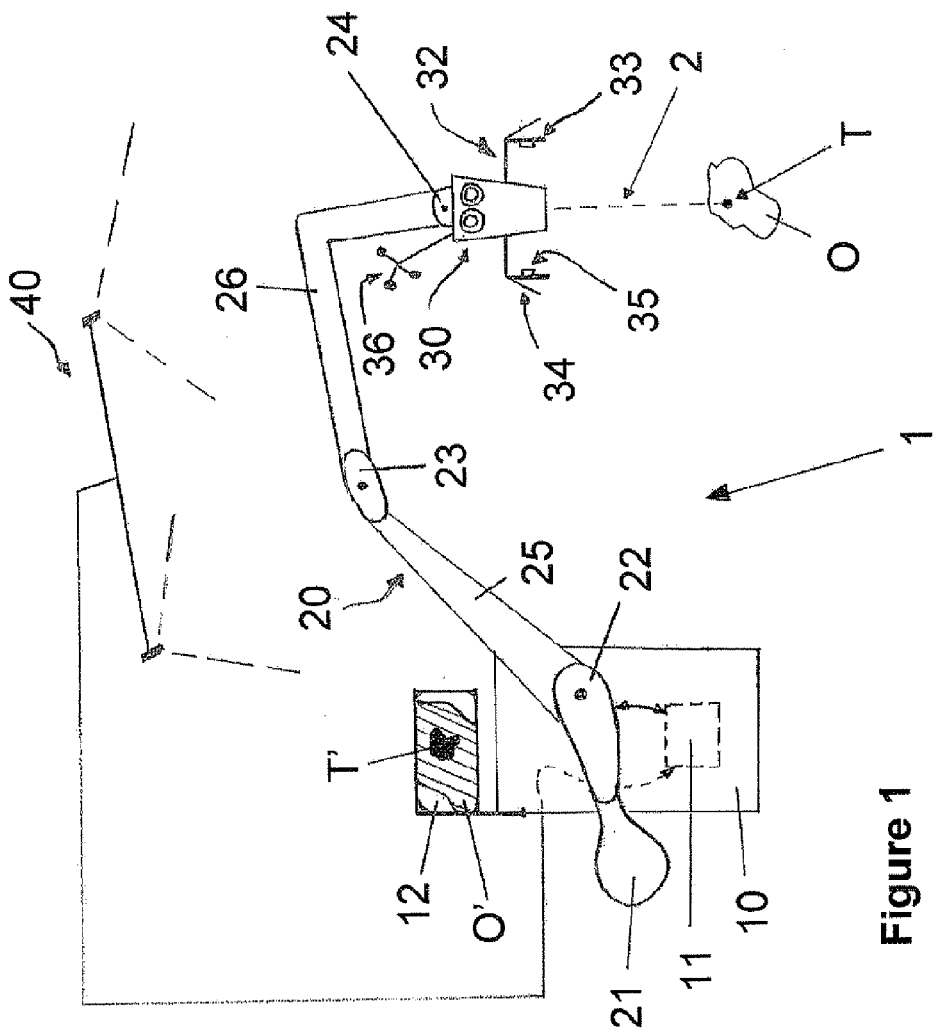

CONTROLLING A SURGICAL MICROSCOPE

This application is a national phase of International Application No. PCT/EP2010/053654 filed Mar. 22, 2010 and published in the English language.

The present invention relates to controlling a surgical microscope. The use of a surgical microscope together with a surgical navigation system has been described in general terms in DE 196 39 615 A1, which suggests that by integrating a surgical navigation system and a surgical microscope, instrument tips or treatment targets can be automatically focussed from different viewing directions.

It is the object of the present invention to provide a method for controlling a surgical microscope, which makes optimum use of the possibility of moving the microscope's optical system within a position tracking environment, in particular in connection with a surgical navigation system.

To this end, the present invention provides a method for controlling a surgical microscope in accordance with claim 1. The sub-claims define advantageous embodiments of the invention.

In the method according to the present invention, the position of the optical system of the microscope is tracked within an operating space by a position tracking system, i.e. the position and/or orientation of the optical system is determined. The carrier supporting or holding said optical system can be moved by means of a motorized carrier moving system. In accordance with the present invention, the line of sight of the optical system is automatically set by moving the optical system carrier, wherein the line of sight is aligned with a predefined direction in said operating space.

In other words, the motorized carrier moving system is controlled in such a way that the carrier for the optical system aligns said system so that its line of sight coincides with a line of sight which has previously been determined, for example one which has been found to be advantageous or particularly suitable for a given situation.

The present invention advantageously makes optimum use of the facilities in situ, namely the positional tracking of the optical system and its mobility. Using the method of the present invention, the user of the microscope can not only very quickly focus on a certain point or target using the microscope's optical system, but can also focus on said point from a previously determined direction, for example the most advantageous direction. Using the microscope, the target can be viewed together with all the important structures in its vicinity which might be covered or not visible when looking from another direction. The surroundings in the operating room can also be taken into consideration when positioning the microscope in such a way that its components do not interfere with other medical devices in the vicinity of the patient.

For the purposes of the present description, the term "line of sight" refers to a virtual line starting from the microscope's optical system and oriented in the viewing direction of the optical system. If the optical system of the microscope is focussed on a target, the "line of sight" extends between the optical system and such a target (or a target point).

In one embodiment of the method of the invention, the predefined direction is defined in the position tracking system, which in turn communicates with a microscope-internal control system which controls the carrier moving system. In other words, the control commands can be processed by a control system which is provided as an integral part of the surgical microscope. In general terms, the control system for the microscope can of course also be provided as a microscope-external control system. The control system could for example be a medical navigation system, or at least a part of one, which is connected to the carrier moving system in order to communicate movement commands or signals.

A tracking system for monitoring the spatial position of the microscope's optical system can be provided in different embodiments. One possibility involves providing a microscope-external tracking system which comprises a position sensor for tracking a reference on the microscope or its optical system. The sensor can for example be a camera or camera system. In general, any known tracking system such as is usually associated with medical navigation systems can be used as an external tracking system in accordance with this embodiment. This includes active or passive, optical (infrared) and/or magnetic tracking systems.

In accordance with another embodiment, the tracking system can be a microscope-internal tracking system, i.e. a system which records and stores the movements of the optical system by monitoring the movements of the optical system carrier and/or the carrier moving system. In particular, a number of sensors can be used on the optical system carrier, specifically joint position sensors on at least one of the joints of an articulated carrier arm. This embodiment provides an advantageously self-contained system which is not dependent on the availability of an external tracking system, although these two systems (external and internal) could be combined in order to achieve higher precision or redundancy.

There are various ways of predefining a direction for the desired line of sight. Said direction can be a direction which has previously been used with the microscope or which has been identified as being particularly advantageous by other means. In one variant, the predefined direction is predefined by manual adjustment and is stored in a memory associated with a microscope-internal control system which controls the carrier moving system. Surgical microscopes usually have handles using which the optical system can be moved to a desired position. In many cases, these movements are motor-assisted. In accordance with the embodiment mentioned above, the microscope can be placed in a position which is regarded as being advantageous by manually moving the optical system into a certain position. A "store" command can be issued and the advantageous position can be stored, either by storing the position of the (joints of) the carrier moving system or by means of the external tracking system. This predefined position and viewing direction will then be available at all times for subsequent use.

On the other hand, the predefined direction can also be predefined on the basis of inputs made on the microscope-internal control system which controls the carrier moving system, in particular via an input device on the microscope such as a control panel. Another option is to predefine the direction by means of a surgical navigation system which is associated with the position tracking system and/or the carrier moving system, wherein the predefined position is relayed from a navigation system to the microscope-internal control system. Such a method is advantageous if the microscope is used in a surgical navigation environment anyway.

The line of sight can be set so as to be aligned with a trajectory which points towards a target, in particular a target on an object, specifically a part of a patient's body which is tracked in the operating space. The patient can be tracked by the same tracking system as is used for tracking the position of the microscope's optical system.

Another way of setting the line of sight is to align it in such a way that it intersects a plane, which is defined in the operating space, at a predefined angle, in particular orthogonally.

In accordance with one embodiment of the present invention, the line of sight is set when a control signal is issued by a user via input means on a microscope-internal control system which controls the carrier moving system. On the other hand, such a control signal can also be issued via input means on a surgical navigation system which communicates with the microscope-internal control system.

In one preferred embodiment, the line of sight is set by re-aligning the line of sight of the optical system to a previously set trajectory. Such a trajectory can have been previously set by a control input on the microscope-internal control system and/or on the surgical navigation system being used and/or simply by storing a certain position after the optical system has been manually moved to a certain position and into a certain orientation.

Controlling the alignment movement with respect to finding its aligned operating position can be supported in different ways. One way is to use the external or internal position tracking system, as mentioned above. Additionally or alternatively, the aligned operating position can be found using an optical analysis of image information in the image taken by a microscope-internal camera (which can be associated with the optical system of the microscope). In particular, patterns and/or shapes of the target or its surroundings can be captured and identified. If a computer-assisted graphical analysis indicates that the image contains a number of structures (for example, tissue structures) "in their correct places", then the alignment will be regarded as having been completed.

The present invention also relates to a program which, when it is running on a computer or is loaded onto a computer, causes the computer to perform a method as described herein in various embodiments. It also relates to a computer program storage medium which comprises such a computer program.

The invention will now be described in more detail by referring to a particular embodiment and to the attached drawings. It should be noted that each of the features of the present invention referred to herein can be implemented separately or in any expedient combination. In the drawings:

FIG. 1 shows a schematic depiction of a surgical microscope which can be used in a method in accordance with the present invention; and FIG. 2 shows a more detailed depiction of an optical system of a surgical microscope such as for example that of FIG. 1.

A microscope such as can be used with the method of the present invention is schematically shown in FIG. 1 and has been given the reference numeral 1. The components of the microscope 1 are supported on a stand 10. The stand 10 supports an articulated arm 20 which will be described in detail further below and which in turn supports the microscope's optical system 30 at its distal end. In the highly integrated embodiment which is schematically shown in FIG. 1, the microscope stand 10 also supports the components of a surgical navigation system, indicated by a box consisting of broken lines and provided with the reference numeral 11. The surgical navigation system 11 is connected to a camera tracking system 40 comprising two cameras which can monitor and track the spatial position of certain objects such as a reference array 36 attached to the optical system 30. Images captured by the optical system 30 and/or images created by the navigation system are shown on the monitor 12 which is also supported by the stand 10. The double-headed arrow connecting the navigation system 11 and the articulated arm 20 is intended to show that the navigation system can be used as a controlling unit for the movement of the articulated arm 20 and that movements made by the articulated arm 20 can in turn be detected and input back into the navigation system for processing. It should be noted that, instead of controlling in connection with a navigation system 11, a microscope-internal control unit which operates independently of a navigation system could also be used.

The articulated arm 20 comprises a counterweight 21 and a first joint 22 at which the arm 20 is connected via a hinge to the stand 10. The other elements of the arm 20 are the first beam 25, the second joint 23, the second beam 26 and the third joint 24 which connects the optical system 30 to the second beam 26 via a hinge. The joints 22, 23 and 24 collectively constitute a system for moving the articulated arm 20 (i.e. the carrier of the optical system 30). The joints 22, 23 and 24 comprise motors which assist the joints 22, 23 and 24 in their movement, in order to make it easier for a person to move and re-arrange the optical system 30.

The user moves the optical system 30 by grasping the handles 33 at the end of a handle bar 32 which is attached to the optical system 30. These elements of the optical system 30 are shown in greater detail in FIG. 2. It can be seen in FIG. 1 that the handles 33 have brake-release bars 34. During use, the articulated arm 20 is held in place by brake elements (not shown) provided in the joints 22, 23 and 24, and in order to change the position of the optical system 30, the user has to pull on the brake-release bars 34 when gripping the handles 33. The joints are then released, and the system 30 can be moved with the assistance of the motors in the joints 22, 23 and 24. The system 30 can thus be moved to a desired position for viewing a target T on an object O. Control buttons 35 are shown on the handles 33 in FIG. 1 and can be used to make control inputs such as "store the current position of the optical system 30 as a predefined position".

It is possible to use a specific software interface, provided with the microscope, to initialize predefined movements by means of and within the framework of a navigation software application which is run on a surgical navigation system such as the navigation system 11. The navigation system can of course also be a separate navigation system (used for other navigation purposes) which is connected to the microscope by communications equipment.

When performing a method according to one embodiment of the present invention, a user would at some time during the beginning of an operation grasp the handles 33 of the optical system 30, release the brakes using the release bars 34 and move the optical system 30 until the line of sight 2 is set such that a target T on an object O (for example, a tumor on a part of a patient's body) can be viewed from an optimum viewing direction. The user would then press the button 35 to issue a "store" command to the navigation system 11. The position and orientation of the optical system 30 would then be detected by means of the tracking system 40 and the reference array 36 attached to the optical system 30. This position and orientation would then be stored by the navigation system 11, and the line of sight 2 would thus be stored and set as a predefined direction.

The surgeon will then continue with the operation and may subsequently wish to examine the target T again. The present invention then advantageously enables the surgeon not only to easily find the target T again and to focus on it, but also to examine the target T from exactly the same viewing direction as before, by re-aligning the optical system 30 in the predefined direction, such that the line of sight 2 coincides with the stored orientation. On the one hand, this improves the surgeon's ability to check the outcome of the operation from comparable views; on the other hand, automatically re-aligning the optical system 30 to a predefined viewing direction enables such re-examination to be performed in a precise and time-efficient manner.

In the embodiment mentioned above, the predefining and re-aligning steps are both performed with the aid of the tracking system 40, the navigation system 11 and the reference array 36. However, it is possible to perform the method of the present invention without navigational support, or at least without the support of an external tracking system such as is shown in FIG. 1.

To this end, the joints 22, 23 and 24 can be equipped with position sensors, and the microscope can comprise an internal control system which monitors the position sensors in the joints 22, 23 and 24 and controls the motors in said joints. In a very simple embodiment of this scenario, a line of sight would be predefined as an advantageous orientation or viewing direction by storing the position of the joints 22, 23 and 24. Some time later during the operation, the surgeon could then enter a re-alignment command (via the buttons 35 or a control panel for the microscope-internal control system). The articulated arm 20 would then return to the stored position, with the aid of the motors and the position sensors in the joints 22, 23 and 24. The line of sight of the optical system 30 is thus automatically set in such a way that it is re-aligned with the previously stored viewing direction. The surgeon can thus obtain a comparable view of the target T by looking into the optical system 30 or by looking at the image representations T' and O' on the microscope's monitor 12.

The joint sensor system (and the tracking system 40 discussed above) can operate using a coordinate system in which all the movements are monitored and detected or controlled. To this end, it can be advantageous to set initial values or zero values or to use calibration points. Such a calibration can be seen in FIG. 2, in which the line of sight 2 is directed onto the central point of a calibration reference array 42 of a navigation/tracking system, the position of which his known, such that a zero point of a coordinate system is for example set.

The movement of the microscope in all the embodiments can be initiated by various methods, i.e. for example by command inputs on the microscope itself (using the button 35 or a control panel) or by a navigation software application which is run on a navigation system used during the operation. The microscope will then move itself in the X-axis, Y-axis and Z-axis directions. The desired location of the microscope can be reached either using position information provided by the navigation system via a specified microscope interface or position information provided by the joint position sensors, or by identifying patterns or shapes using the microscope's camera unit, until the microscope has aligned itself along the predefined trajectory or perpendicular to a given predefined plane.

If the microscope is used without a navigation system, it is for example possible to define one or more specific positions of the microscope, for example using the microscope handle button 35. The microscope's control system can then for example connect two of the defined positions and thus set or define a trajectory to which it then re-aligns itself. In another embodiment, the microscope can use a built-in sensor or specific position values of the built-in motors to align its line of sight perpendicular to any given plane.

The invention claimed is:

1. A method for controlling a surgical microscope, wherein the position of the optical system of the microscope is tracked within an operating space by a position tracking system, wherein the optical system carrier can be moved by means of a motorized carrier moving system, wherein the line of sight of the optical system is automatically set by moving the optical system carrier, wherein pattern and/or shape information is determined by an optical image analysis of an image of an associated object in the line of sight, wherein the line of sight is automatically re-aligned with a predefined direction in said operating space responsive to receiving a re-alignment command entered via a control button provided on a handle of the surgical microscope for manually moving the microscope so that the line of sight of the optical system coincides with a line of sight which has previously been determined selectively in accordance with the determined pattern and/or shape information.

2. The method according to claim 1, wherein the predefined direction is defined in the position tracking system, which in turn communicates with a microscope-internal control system which controls the carrier moving system.

3. The method according to claim 1, wherein the tracking system is a microscope-external tracking system which comprises a sensor and a reference on the microscope or its optical system.

4. The method according to claim 1, wherein the tracking system is a microscope-internal tracking system which comprises at least one sensor on the optical system carrier.

5. The method according claim 1, wherein the predefined direction is predefined by manual adjustment and is stored in a memory associated with a microscope-internal control system which controls the carrier moving system.

6. The method according to claim 1, wherein the predefined direction is predefined on the basis of inputs made on the microscope-internal control system which controls the carrier moving system.

7. The method according to claim 1, wherein the predefined direction is predefined by means of a surgical navigation system which is associated with the position tracking system and/or the carrier moving system, and wherein the predefined position is relayed from the navigation system to the microscope-internal control system which controls the carrier moving system.

8. The method according to claim 1, wherein the line of sight is set so as to be aligned with a trajectory which points towards a target.

9. The method according to claim 1, wherein the line of sight is set by being aligned in such a way that it intersects a plane which is defined in the operating space at a predefined angle.

10. The method according to claim 1, wherein the line of sight is set when a control signal is issued by a user via input means on a microscope-internal control system which controls the carrier moving system.

11. The method according to claim 1, wherein the line of sight is set when a control signal is issued by a user via input means on a surgical navigation system which communicates with the microscope-internal control system which controls the carrier moving system.

12. The method according to claim 1, wherein the line of sight is set by re-aligning the line of sight of the optical system to a trajectory previously set by a control input on the microscope-internal control system and/or on a surgical navigation system.

13. The method according to claim 1, wherein controlling the alignment movement with respect to finding its aligned operating position is supported by: the external or internal position tracking system; and/or an optical analysis of image information comprising patterns and/or shapes, in the image taken by a microscope-internal camera.

14. A non-transitory computer readable storage medium storing a computer program which, when running on a computer or loaded onto a computer, causes the computer to perform a method for controlling a surgical microscope, wherein the position of the optical system of the microscope is tracked within an operating space by a position tracking system, wherein the optical system carrier can be moved by means of a motorized carrier moving system, wherein pattern and/or shape information is determined by an optical image analysis of an image of an associated object in the line of sight, wherein the line of sight of the optical system is automatically set by moving the optical system carrier, wherein the line of sight is automatically re-aligned with a predefined direction in said operating space responsive to receiving a re-alignment command entered via a control button provided on a handle of the surgical microscope for manually moving the microscope so that the line of sight of the optical system coincides with a line of sight which has previously been determined selectively in accordance with the determined pattern and/or shape information.

15. The method according to claim 3, wherein the microscope-external tracking system is a camera system.

16. The method according to claim 4, wherein the microscope-internal tracking system comprises a plurality of sensors including joint position sensors on at least one of the joints of an articulated carrier arm.

17. The method according to claim 8, wherein the line of sight is set so as to be aligned with a trajectory which points towards a target on an object, wherein the object is a part of an associated patient's body which is tracked in the operating space.

18. The method according to claim 9, wherein the line of sight orthogonally intersects the plane defined in the operating space.

19. A method for controlling a surgical microscope, the method comprising:
   tracking, by a position tracking system, a position of an optical system of the surgical microscope within an operating space;
   selectively moving a carrier of the optical system by a motorized carrier moving system;
   automatically setting a line of sight of the optical system by moving the optical system carrier;
   determining pattern and/or shape information by an optical image analysis of an image of an associated object in the line of sight;
   automatically re-aligning the line of sight with a predefined direction in said operating space responsive to a re-alignment command received by the surgical microscope via a control button provided on a handle of the surgical microscope for manually moving the microscope, so that the automatically re-aligned line of sight of the optical system coincides with a line of sight of the optical system which has previously been determined selectively in accordance with the determined pattern and/or shape information.

20. A surgical microscope comprising:
   an optical system disposed in an operating space, the optical system comprising a camera;
   a motorized carrier system configured to support and selectively move the optical system to one or more selected positions relative to an associated object orienting a line of sight of the camera at a target on the associated object;
   a handle operatively coupled with the optical system, the handle being configured to be grasped by an associated human user of the surgical microscope for manually moving the optical system into the one or more selected positions relative to the associated object;
   a control button on the handle, the button being operable by the associated user to generate a store position command signal representative of the button being actuated by the associated user with the optical system supported by the carrier system held by the associated user at a desired position and orientation providing the camera with a desired line of sight relative to the target on the associated object, wherein the optical system is responsive to the store position command signal to acquire a first image of the associated object and to store the desired position and orientation of the optical system as a predefined desired position and orientation; and
   an optical analysis system operatively coupled with the optical system, wherein the optical analysis system is responsive to the store position command signal to selectively capture and identify pattern and/or shape information in the first image of the associated object acquired by the optical system,
   wherein the motorized carrier system is responsive to a re-alignment command signal received from one or more of the control button on the handle, the optical analysis system or an associated tracking system monitoring a spatial position of the optical system in the operating space, to return the optical system from a position and orientation other than the desired position and orientation to the predefined desired position and orientation whereat the line of sight of the camera coincides with the stored desired line of sight.

21. The surgical microscope according to claim 20, further comprising:
   an external tracking system configured to monitor the spatial position of the optical system in the operating space, the external tracking system comprising a reference array operatively coupled with the optical system, and two or more tracking cameras configured to track and determine a position and orientation of the reference array operatively coupled with the optical system,
   wherein the motorized carrier system is responsive to a re-alignment command signal received from the external tracking system monitoring the spatial position of the optical system in the operating space to return the optical system to the predefined desired position and orientation whereat the line of sight of the camera coincides with the stored desired line of sight.

22. The surgical microscope according to claim 20, further comprising:
   an internal tracking system configured to monitor the spatial position of the optical system in the operating space, the internal tracking system comprising a navigation system and a plurality of position sensors located on joints pivotally connecting beams of the motorized carrier system, the plurality of position sensors generating position signals representative of relative positions of the connecting beams of the motorized carrier system and the navigation system receiving the position signals and determining a position and orientation of the optical system supported by the motorized carrier system,
   wherein the motorized carrier system is responsive to a re-alignment command signal received from the internal tracking system monitoring the spatial position of the optical system in the operating space to return the optical system to the predefined desired position and orientation whereat the line of sight of the camera coincides with the stored desired line of sight.

23. The surgical microscope according to claim 20, wherein:
   the optical analysis system comprises a computer-assisted graphical analysis system configured to capture and identify pattern and/or shape information in a second image of the associated object acquired by the optical system in the position and orientation other than the desired position and orientation and compare the captured and identified pattern and/or shape information in the second image with the captured and identified pattern and/or shape information in the first image to determine an alignment between the pattern and/or shape information in the second image with the pattern and/or shape information in the first image, and the motorized carrier system is responsive to a re-alignment command signal received from the optical analysis system to return the optical system to the predefined desired position and orientation in accordance with the determined alignment, whereat the line of sight of the camera coincides with the stored desired line of sight.

* * * * *